(12) United States Patent
Levorse, Jr. et al.

(10) Patent No.: US 8,168,834 B2
(45) Date of Patent: May 1, 2012

(54) 4-ALKYL 1-(3-METHOXY-2-PROPEN-1-YL) BENZENE COMPOUNDS AND THEIR USE IN PERFUME COMPOSITIONS

(75) Inventors: Anthony T. Levorse, Jr., Westfield, NJ (US); Robert P. Belko, Monroe, NJ (US); Benjamin Amorelli, Farmingdale, NJ (US); Anubhav P. S. Narula, Hazlet, NJ (US); Michael G. Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 383 days.

(21) Appl. No.: 12/619,176

(22) Filed: Nov. 16, 2009

(65) Prior Publication Data

US 2011/0118509 A1 May 19, 2011

(51) Int. Cl.
*C07C 43/166* (2006.01)
*A61K 8/33* (2006.01)
*C11D 3/50* (2006.01)

(52) U.S. Cl. ..................................... 568/626

(58) Field of Classification Search .................. None
See application file for complete search history.

(56) References Cited

U.S. PATENT DOCUMENTS 3,943,943 A * 3/1976 Cartwright et al. ........... 131/276

OTHER PUBLICATIONS

Ohloff, G. et al. "Conformationally Controlled Odor Perception in 'Steroid-type' Scent Molecules." Helvetica Chimica Acta (1983) 66(5): 1343-1354.
Verlhac, J.B. et al. "An Easy Access to β-Acyl- and β-Arylpropionaldehydes Through a New Silylated Organotin Homoenolate Equivalent." J. Chem. Soc. (1988) 7: 503-504.
Ishikawa, Y. et al. "Molecular Orbital Approach to Odor Molecules: Normal Fatty Acids and Cyclamenaldehydes." Int. J. Quantum Chem. (2000) 79(2): 101-108.

* cited by examiner

*Primary Examiner* — Rosalynd Keys
(74) *Attorney, Agent, or Firm* — Elizabeth M. Quirk; XuFan Tseng; Joseph F. Leightner

(57) ABSTRACT

The present invention is directed to novel 4-alkyl 1-(3-methoxy-2-propen-1-yl)benzene compounds and a method of improving, enhancing or modifying a fragrance formulation through the addition of an olfactory acceptable amount of the novel compounds.

10 Claims, No Drawings

4-ALKYL 1-(3-METHOXY-2-PROPEN-1-YL) BENZENE COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances. For example, benzene compounds that differ slightly in substituents possess completely different odor profiles [Ishikawa, et al., International Journal of Quantum Chemistry 79: 101-108 (2000)]. In the case of tert-butyl cyclohexanes, the odor is said to be dependent on the compounds' conformation and therefore analogs adopting same conformation possess similar odor. Accordingly, many trans-compounds are shown to share pronounced urine-perspiration-type odor, while the corresponding cis-compounds are odorless or at the most possess weak and undefinable flowery or woody odor. However, some other trans- and cis-tert-butyl cyclohexanes are shown to possess opposite sensory activities [Ohloff, et al., Helvetica Chimica Acta 66, Fasc. 5: 1343-1354 (1983)]. Thus, it is hard for those with skill in the art to predict a given structure would be effective in sensory activities. Identifying desirable fragrance chemicals continues to pose difficult challenges.

SUMMARY OF THE INVENTION

The present invention provides novel chemicals and their unexpected advantageous use in enhancing, improving or modifying the fragrance of perfumes, colognes, toilet waters, personal products and the like.

In one embodiment of the present invention, novel compounds represented by Formula I are provided:

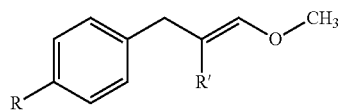

Formula I wherein R represents a $C_1$-$C_4$ alkyl group and R' represents hydrogen or methyl.

In another embodiment of the present invention, a method of improving, enhancing or modifying a fragrance formulation through the addition of an olfactory acceptable amount of a Formula I compound is provided.

In another embodiment of the present invention, novel compounds represented by Formula II are provided:

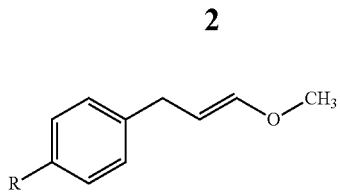

Formula II wherein R represents a $C_1$-$C_4$ alkyl group.

In another embodiment of the present invention, a method of improving, enhancing or modifying a fragrance formulation through the addition of an olfactory acceptable amount of a Formula II compound is provided.

In another embodiment of the present invention, novel compounds represented by Formula III are provided:

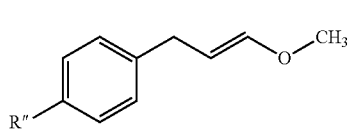

Formula III wherein R" represents a $C_2$-$C_4$ alkyl group.

In another embodiment of the present invention, a method of improving, enhancing or modifying a fragrance formulation through the addition of an olfactory acceptable amount of a Formula III compound is provided.

These and other embodiments of the present invention will be apparent by reading the following specification.

DETAILED DESCRIPTION OF THE INVENTION

It is known to those with the skill in the art that Formula I as defined above provides the following novel compounds:

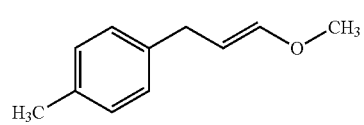

Formula IV

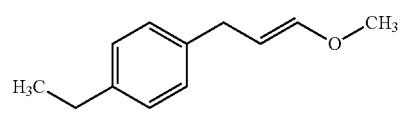

Formula V

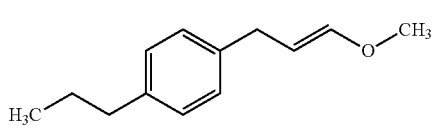

Formula VI

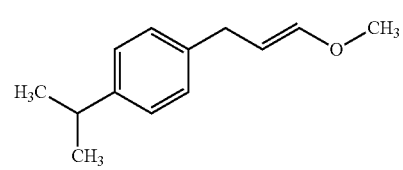

Formula VII

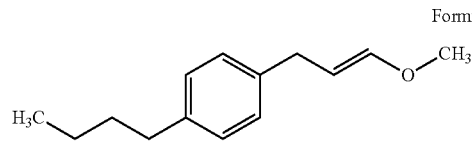

Formula VIII

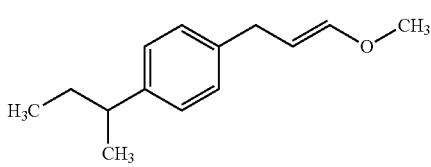
Formula IX

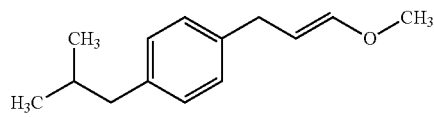
Formula X

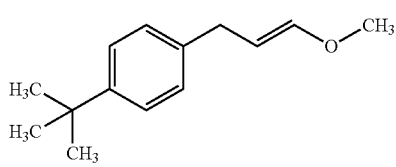
Formula XI

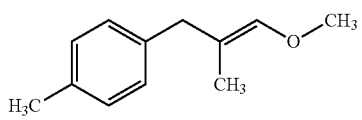
Formula XII

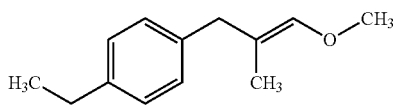
Formula XIII

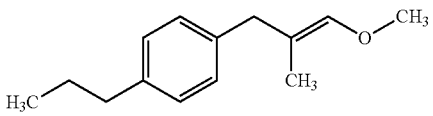
Formula XIV

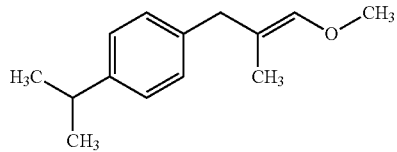
Formula XV

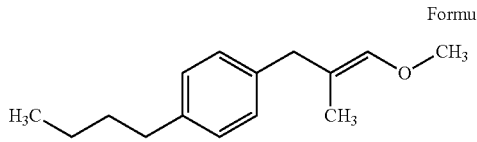
Formula XVI

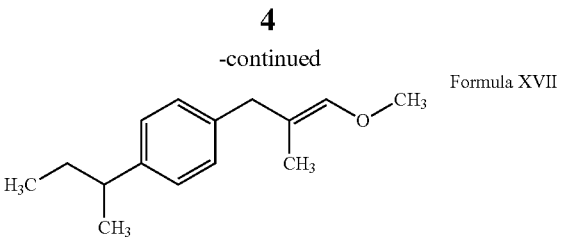
Formula XVII

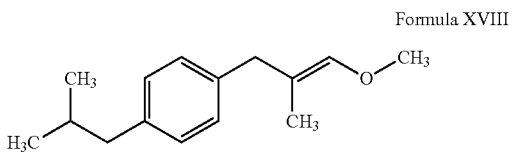
Formula XVIII

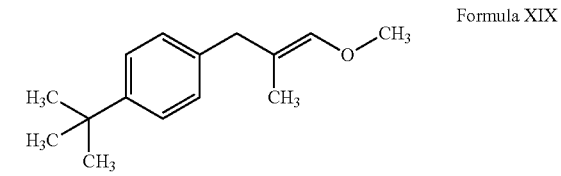
Formula XIX

Those with the skill in the art will recognize that:

Formula IV represents 4-methyl 1-(3-methoxy-2-propen-1-yl)benzene;

Formula V represents 4-ethyl 1-(3-methoxy-2-propen-1-yl)benzene;

Formula VI represents 4-propyl 1-(3-methoxy-2-propen-1-yl)benzene;

Formula VII represents 4-isopropyl 1-(3-methoxy-2-propen-1-yl)benzene;

Formula VIII represents 4-butyl 1-(3-methoxy-2-propen-1-yl)benzene;

Formula IX represents 4-sec-butyl 1-(3-methoxy-2-propen-1-yl)benzene;

Formula X represents 4-isobutyl 1-(3-methoxy-2-propen-1-yl)benzene;

Formula XI represents 4-tert-butyl 1-(3-methoxy-2-propen-1-yl)benzene;

Formula XII represents 4-methyl (3-methoxy-2-methylallyl)benzene;

Formula XIII represents 4-ethyl (3-methoxy-2-methylallyl)benzene;

Formula XIV represents 4-propyl (3-methoxy-2-methylallyl)benzene;

Formula XV represents 4-isopropyl (3-methoxy-2-methylallyl)benzene;

Formula XVI represents 4-butyl (3-methoxy-2-methylallyl)benzene;

Formula XVII represents 4-sec-butyl (3-methoxy-2-methylallyl)benzene;

Formula XVIII represents 4-isobutyl (3-methoxy-2-methylallyl)benzene; and

Formula XIX represents 4-tert-butyl (3-methoxy-2-methylallyl)benzene.

The compounds of the present invention can be prepared from 3-(4-alkyl-phenyl)-propionaldehydes, which are first synthesized via the Hoaglin-Hirsch reaction using corresponding 4-alkyl benzaldehydes (commercially available from Mitsubishi Gas Chemical Company, Inc.). The reaction steps can be depicted by general Schemes 1 and 2 shown as follows:

Scheme 1. Preparation of 3-(4-alkyl-phenyl)-propionaldehydes.

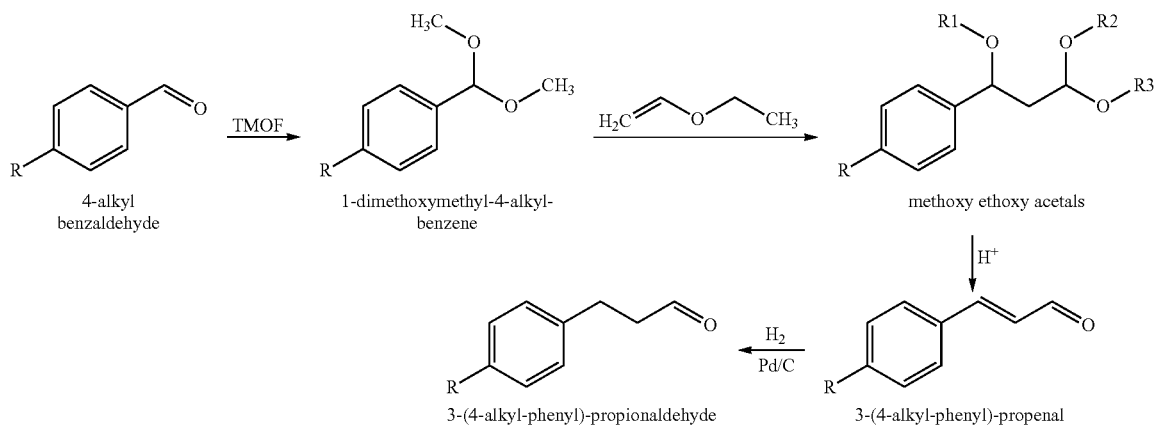

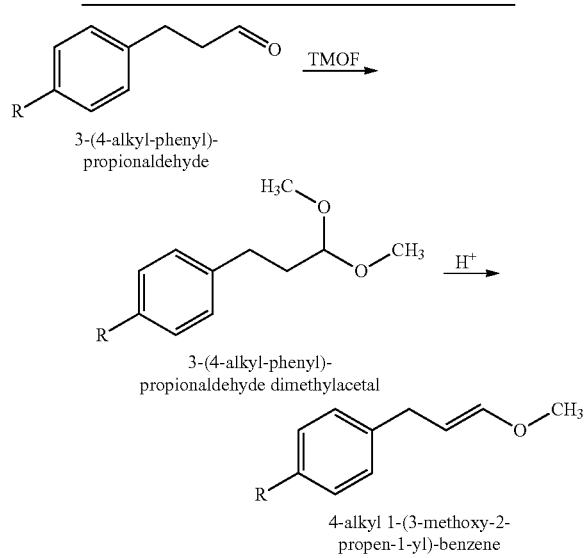

wherein R is defined as above;
$R_1$, $R_2$, and $R_3$ represent independently methyl or ethyl;
TMOF represents trimethyl orthoformate; and
Pd/C represents palladium carbon catalyst.

Those with skill in the art will recognize that the 1,4-substituted aromatic rings contained in the compounds of the present invention give rise to a number of trans- and cis-isomers. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 10 weight percent, more preferably from about 0.5 to about 8 weight percent, and even more preferably from about 1 to about 7 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, the compounds of the present invention provide unexpected strong muguet and green characteristics and make the fragrance formulation more desirable and noticeable. The odor qualities found in the compounds of the present invention assist in beautifying and enhancing the finished accord and improve the performance of other materials in the fragrance formulation.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, Kg is understood to be kilogram, g is understood to be gram, and mmHg be millimeters (mm) of mercury (Hg). IFF as used in the examples is understood to mean International Flavors & Fragrances Inc., New York, N.Y., USA.

Example I with saturated sodium carbonate (500 mL). The crude intermediate products methoxy ethoxy acetals were obtained, which were contained in the organic layer and confirmed by NMR analysis. Crude methoxy ethoxy acetals were hydrolyzed in the presence of water (500 mL) containing hydrochloric acid (37%, 50 g) at 90° C. for 5 hours and further catalytically hydrogenated in 2-propanol (200 mL) using palladium on carbon (5%, 1 g) and hydrogen in a 1 L zipper autoclave to provide the product 3-(4-propyl-phenyl)-propionaldehyde (1.008 Kg), which had a boiling point of 115° C. at a pressure of 6 mmHg.

The NMR analysis of the intermediate products methoxy ethoxy acetals was the following:

$^1$HNMR: 0.94 ppm (t, 3H, J=7.02 Hz), 1.13-1.27 ppm (m, 9H), 1.529-1.68 ppm (m, 2H), 1.84-1.91 ppm (m, 1H), 2.06-2.14 ppm (m, 1H), 2.55-2.59 ppm (m, 2H), 2.66 ppm (t, 2H, J=7.59 Hz), 3.17 ppm (s, 3H), 3.30 ppm (s, 3H), 3.33 ppm (s, 3H), 3.35-3.67 ppm (m, 6H), 4.19-4.60 ppm (m, 2H), 7.15 ppm (d, 2H, J=5.94 Hz), 7.21 ppm (d, 2H, J=7.33 Hz), 7.32 ppm (d, 2H, J=7.85 Hz), 7.78 ppm (d, 2H, J=7.94 Hz), 9.95 ppm (s, 1H).

The NMR analysis of 3-(4-propyl-phenyl)-propionaldehyde was the following:

$^1$HNMR: 0.93 ppm (t, 3H, J=7.34 Hz), 1.62 ppm (m, 2H), J=7.52 Hz), 2.55 ppm (t, 2H, J=7.66 Hz), 2.75 ppm (t, 2H, J=7.56 Hz), 2.92 ppm (t, 2H, J=7.56 Hz), 7.10 ppm (s, 4H), 9.81 ppm (s, 1H)

The compound 3-(4-propyl-phenyl)-propionaldehyde was described as having floral, muguet, and green notes.

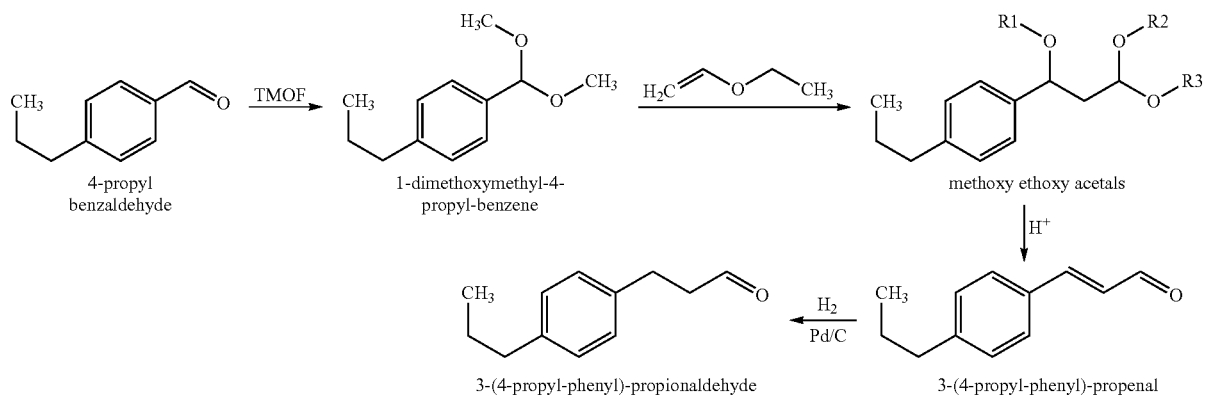

Preparation of 3-(4-propyl-phenyl)-propionaldehyde: A reaction flask was charged with 4-propyl benzaldehyde (1.064 Kg, commercially available from Mitsubishi Gas Chemical Company, Inc.), methanol (500 mL), and trimethyl orthoformate (TMOF) (1.144 Kg, commercially available from Sigma-Aldrich, Inc.). The reaction mass was cooled to −10 to 0° C. and hydrochloric acid (37%, 1 g) was added in one portion. The reaction was instantaneous and the temperature was allowed to rise to 25° C. for over 30 minutes. The reaction mass was then quenched with sodium acetate (20 g) and the solvent was removed by evaporation. The crude intermediate product 1-dimethoxymethyl-4-propyl-benzene (1.388 Kg) was obtained and charged to a second reaction flask at 25° C. Boron trifluoride etherate (1 g, commercially available from Sigma-Aldrich, Inc.) was added. Ethyl vinyl ether (684 g, commercially available from Sigma-Aldrich, Inc.) was then fed for over 4 hours with the temperature maintained at 25-30° C. The reaction mass was quenched Example II

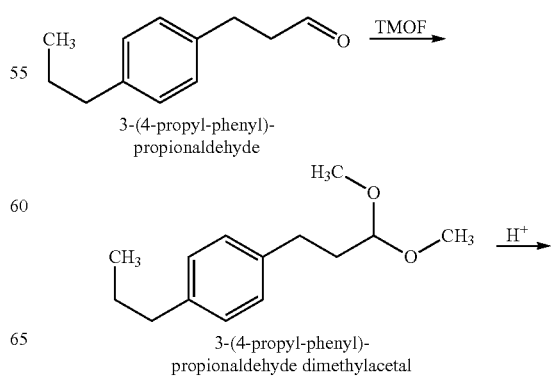

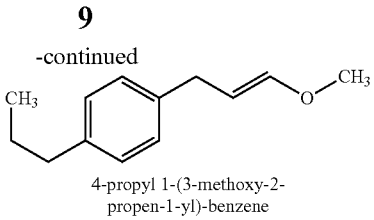

4-propyl 1-(3-methoxy-2-
propen-1-yl)-benzene

Preparation of 4-propyl 1-(3-methoxy-2-propen-1-yl)benzene (Formula IV): A reaction flask was charged with 3-(4-propyl-phenyl)-propionaldehyde (147 g, prepared as above), methanol (500 mL), and TMOF (90 g). The reaction mass was cooled to 0° C. and hydrochloric acid (37%, 1 g) was added in one portion. The reaction was exothermic and the temperature rose to 23° C. The reaction mass was quenched with sodium methoxide in methanol (25%, 10 g) and the solvent was removed by evaporation. The crude intermediate product 3-(4-propyl-phenyl)-propionaldehyde dimethylacetal was provided and confirmed by the NMR analysis. 3-(4-Propyl-phenyl)-propionaldehyde dimethylacetal was further treated with phosphoric acid (10 g) and pyridine (8 g) at 200° C. The reaction mass was aged for 4 hours, during which methanol was recovered in a Dean Stark trap. The reaction mass was then cooled and washed with aqueous sodium carbonate solution. Fractional distillation of the organic layer afforded the product 4-propyl 1-(3-methoxy-2-propen-1-yl)benzene (80 g), which had a boiling point of 101° C. at a pressure of 3 mmHg.

The NMR analysis of the intermediate product 3-(4-propyl-phenyl)-propionaldehyde dimethylacetal was the following:

$^1$HNMR: 0.93 ppm (t, 3H, J=7.34 Hz), 1.62 ppm (m, 2H, J=7.49 Hz), 1.88-1.93 ppm (m, 2H), 2.55 ppm (t, 2H, J=7.66 Hz), 2.62-2.66 ppm (m, 2H), 3.33 ppm (s, 6H), 4.37 ppm (t, 1H, J=5.74 Hz), 7.10 ppm (d, 4H, J=1.48 Hz)

The NMR analysis of 4-propyl 1-(3-methoxy-2-propen-1-yl)benzene was the following:

$^1$HNMR: 0.91 ppm (d, 3H, J=1.85 Hz, of t, J=7.29 Hz), 1.55-1.63 ppm (m, 2H), 2.49-2.54 ppm (m, 2H), 3.18 ppm (d, ~44% of 2H, J=7.29 Hz), 3.37 ppm (d, ~56% of 2H, J=7.55 Hz), 3.42 ppm (s, ~44% of 3H), 3.51 ppm (s, ~56% of 3H), 4.50-4.55 ppm (m, ~56% of 1H), 4.84 ppm (d, ~44% of 1H, J=12.56 Hz, of t, J=7.21 Hz), 5.91 ppm (d, ~56% of 1H, J=6.09 Hz), 6.34 ppm (d, ~44% of 1H, J=12.58 Hz), 7.02-7.11 ppm (m, 4H)

The compound 4-propyl 1-(3-methoxy-2-propen-1-yl) benzene was described as having muguet, green, and fatty notes.

Example III

Preparation of 4-methyl 1-(3-methoxy-2-propen-1-yl)benzene (Formula II): 4-Methyl 1-(3-methoxy-2-propen-1-yl)benzene was similarly prepared as described in Examples I and II. First, 4-methyl benzaldehyde (140 g, commercially available from Mitsubishi Gas Chemical Company, Inc.) was used to obtain 3-(4-methyl-phenyl)-propionaldehyde (130 g) with a boiling point of 120° C. at a pressure of 21 mmHg. 3-(4-Methyl-phenyl)-propionaldehyde (225 g) was consequently used to provide 4-methyl 1-(3-methoxy-2-propen-1-yl)benzene (139 g) with a boiling point of 117° C. at a pressure of 35 mmHg The NMR analysis of 3-(4-methyl-phenyl)-propionaldehyde was the following:

$^1$HNMR: 2.29 ppm (s, 3H), 2.69 ppm (t, 2H, J=7.32 Hz), 2.88 ppm (t, 2H, J=7.49 Hz), 7.05 ppm (d, 2H, J=8.04 Hz), 7.07 ppm (d, 2H, J=7.92 Hz), 9.74 ppm (s, 1H)

The NMR analysis of 4-methyl 1-(3-methoxy-2-propen-1-yl)benzene was the following:

$^1$HNMR: 2.28 ppm (s, ~46% of 3H), 2.29 ppm (s, ~54% of 3H), 3.19 ppm (d, ~54% of 2H, J=7.31 Hz), 3.37 ppm (d, ~46% of 2H, J=7.41 Hz), 3.47 ppm (s, ~54% of 3H), 3.57 ppm (s, ~46% of 3H), 4.50-4.55 ppm (m, ~46% of 1H), 4.85 ppm (d, ~54% of 1H, J=12.57 Hz, of t, J=7.31 Hz), 5.94 ppm (d, ~46% of 1H, J=6.12 Hz), 6.36 ppm (d, ~54% of 1H, J=12.59 Hz), 7.03-7.10 ppm (m, 4H)

The compound 4-methyl 1-(3-methoxy-2-propen-1-yl) benzene was described as having muguet, green, and fatty notes.

Example IV

Preparation of 4-ethyl 1-(3-methoxy-2-propen-1-yl)benzene (Formula III): 4-Ethyl 1-(3-methoxy-2-propen-1-yl)benzene was similarly prepared as described in Examples I and II. First, 4-ethyl benzaldehyde (925 g, commercially available from Mitsubishi Gas Chemical Company, Inc.) was used to obtain 3-(4-ethyl-phenyl)-propionaldehyde (878 g) with a boiling point of 129° C. at a pressure of 12 mmHg. 3-(4-Ethyl-phenyl)-propionaldehyde (235 g) was consequently used to provide 4-ethyl 1-(3-methoxy-2-propen-1-yl) benzene (128 g) with a boiling point of 120° C. at a pressure of 10 mmHg.

The NMR analysis of 3-(4-ethyl-phenyl)-propionaldehyde was the following:

$^1$HNMR: 1.20 ppm (t, 3H, J=7.61 Hz), 2.59 ppm (q, 2H, J=7.58 Hz), 2.68 ppm (t, 2H, J=7.55 Hz), 2.88 ppm (t, 2H, J=7.52 Hz), 7.06-7.11 ppm (m, 4H), 9.73 ppm (s, 1H)

The NMR analysis of 4-ethyl 1-(3-methoxy-2-propen-1-yl)benzene was the following:

$^1$HNMR: 1.20 ppm (t, ~60% of 3H, J=7.59 Hz), 1.21 ppm (t, ~40% of 3H, J=7.58 Hz), 2.56-2.63 ppm (m, 2H), 3.21 ppm (d, ~40% of 2H, J=7.28 Hz), 3.38 ppm (d, ~60% of 2H, J=7.38 Hz), 3.48 ppm (s, ~40% of 3H), 3.58 ppm (s, ~60% of 3H), 4.52-4.57 ppm (m, ~60% of 1H), 4.87 ppm (d, ~40% of 1H, J=12.56 Hz, of t, J=7.28 Hz), 5.95 ppm (d, ~60% of 1H, J=6.11 Hz), 6.37 ppm (d, ~40% of 1H, J=12.78 Hz), 7.07-7.13 ppm (m, 4H)

The compound 4-ethyl 1-(3-methoxy-2-propen-1-yl)benzene was described as having muguet, green, and fatty notes.

Example V

Preparation of 4-isobutyl 1-(3-methoxy-2-propen-1-yl) benzene (Formula VIII): 4-Isobutyl 1-(3-methoxy-2-propen-1-yl)benzene was similarly prepared as described in Examples I and II. First, 4-isobutyl benzaldehyde (600 g, commercially available from Mitsubishi Gas Chemical Company, Inc.) was used to obtain 3-(4-isobutyl-phenyl)-propionaldehyde (568 g) with a boiling point of 119° C. at a pressure of 5 mmHg. 3-(4-Isobutyl-phenyl)-propionaldehyde (345 g) was consequently used to provide 4-isobutyl 1-(3-methoxy-2-propen-1-yl)benzene (188 g) with a boiling point of 124° C. at a pressure of 4 mmHg.

The NMR analysis of 3-(4-isobutyl-phenyl)-propionaldehyde was the following:

$^1$HNMR: 0.89 ppm (d, 6H, J=6.64 Hz), 1.83 ppm (m, 1H, J=6.74 Hz), 2.43 ppm (d, 2H, J=7.18 Hz), 2.72 ppm (t, 2H, J=7.58 Hz, of d, J=1.15 Hz), 2.90 ppm (t, 2H, J=7.57 Hz), 7.05 ppm (d, 2H, J=8.20 Hz), 7.08 ppm (d, 2H, J=8.19 Hz), 9.77 ppm (t, 1H, J=1.43 Hz)

The NMR analysis of 4-isobutyl 1-(3-methoxy-2-propen-1-yl)benzene was the following:

¹HNMR: 0.89 ppm (d, ~43% of 6H, J=6.59 Hz), 0.90 ppm (d, ~57% of 6H, J=6.59 Hz), 1.81-1.86 ppm (m, 1H), 2.42-2.45 ppm (m, 2H), 3.23 ppm (d, ~57% of 2H, J=7.32 Hz), 3.39 ppm (d, ~43% of 2H, J=7.40 Hz), 3.53 ppm (s, ~57% of 3H), 3.63 ppm (s, ~43% of 3H), 4.54-4.57 ppm (m, ~43% of 1H), 4.90 ppm (d, ~57% of 1H, J=12.58 Hz, of t, J=7.32 Hz), 5.99 ppm (d, ~43% of 1H, J=6.13 Hz), 6.39 ppm (d, ~57% of 1H, J=12.58 Hz), 7.03-7.07 ppm (m, 2H), 7.10-7.13 ppm (m, 2H)

The compound 4-isobutyl 1-(3-methoxy-2-propen-1-yl)benzene was described as having muguet, green, and fatty notes.

Example VI

Preparation of 4-tert-butyl 1-(3-methoxy-2-propen-1-yl)benzene (Formula IX): 4-Tert-butyl 1-(3-methoxy-2-propen-1-yl)benzene was similarly prepared as described in Examples I and II. First, 4-tert-butyl benzaldehyde (commercially available from TCI Company) was used to obtain 3-(4-tert-butyl-phenyl)-propionaldehyde (1.1 Kg), which was consequently used to afford 4-tert-butyl 1-(3-methoxy-2-propen-1-yl)benzene (636 g). The product 4-tert-butyl 1-(3-methoxy-2-propen-1-yl)benzene has a boiling point of 98° C. at a pressure of 1.2 mmHg.

¹HNMR: 1.30 ppm (s, ~40% of 9H), 1.31 ppm (s, ~60% of 9H), 3.24 ppm (d, ~60% of 2H, J=7.36 Hz), 3.39 ppm (d, ~40% of 2H, J=7.47 Hz), 3.53 ppm (s, ~60% of 3H), 3.63 ppm (s, ~40% of 3H), 4.54-4.59 ppm (m, ~40% of 1H), 4.90 ppm (d, ~60% of 1H, J=12.58 Hz, of t, J=7.35 Hz), 5.99 ppm (d, ~40% of 1H, J=6.13 Hz), 6.40 ppm (d, ~60% of 1H, J=12.59 Hz), 7.13-7.17 ppm (m, 2H), 7.28-7.33 ppm (m, 2H)

The compound 4-tert-butyl 1-(3-methoxy-2-propen-1-yl)benzene was described as having muguet, green, and fatty notes.

Example VII

The fragrance formula exemplified as follows demonstrates that a 4-alkyl 1-(3-methoxy-2-propen-1-yl)benzene compound imparts muguet and green characters to a musk fragrance formula.

| Ingredients | Parts* | |
|---|---|---|
| | + | − |
| Allyl Caproate | 10 | 10 |
| Leaf Alcohol | 5 | 5 |
| Kharismal ® | 15 | 15 |
| Seveniff ® | 100 | 100 |
| Alpha Damascone | 5 | 5 |
| Cashmeran ® | 10 | 10 |
| Nebulone ® | 50 | 50 |
| Iso E Super ® | 100 | 100 |
| Phenoxanol ® | 65 | 65 |
| Vivaldie ® | 20 | 20 |
| Verdox ® | 70 | 70 |
| Undecavertol | 5 | 5 |
| Applelide ® | 40 | 40 |
| 4-Propyl 1-(3-methoxy-2-propen-1-yl) benzene (Formula IV) | 45 | — |
| DPG | — | 45 |
| Total | 540 | 540 |

*"+" represents a 4-alkyl 1-(3-methoxy-2-propen-1-yl) benzene compound containing formula; and "−" represents a 4-alkyl 1-(3-methoxy-2-propen-1-yl) benzene compound non-containing formula.

Example VIII

The fragrance formula exemplified as follows demonstrates that a 4-alkyl 1-(3-methoxy-2-propen-1-yl)benzene compound imparts muguet and green characters to a female fragrance formula.

| Ingredients | Parts* | |
|---|---|---|
| | + | − |
| Salicynalva ® | 80 | 80 |
| Delta Damascone | 25 | 25 |
| Gamma Decalactone | 2 | 2 |
| Dimethyloctenol | 10 | 10 |
| Phenyl ethyl alcohol | 20 | 20 |
| Montaverdi ® | 5 | 5 |
| Geraniol | 150 | 150 |
| Linalool | 50 | 50 |
| Iso E Super ® | 123 | 123 |
| Cashmeran ® | 25 | 25 |
| Applelide ® | 100 | 100 |
| Galbascone ® | 15 | 15 |
| Leaf Alcohol | 5 | 5 |
| Globanone ® | 20 | 20 |
| Aldehyde C10 | 30 | 30 |
| Kharismal ® | 25 | 25 |
| Vanillin | 5 | 5 |
| 4-Propyl 1-(3-methoxy-2-propen-1-yl) benzene (Formula IV) | 10 | — |
| DPG | — | 10 |
| Total | 700 | 700 |

*"+" represents a 4-alkyl 1-(3-methoxy-2-propen-1-yl) benzene compound containing formula; and "−" represents a 4-alkyl 1-(3-methoxy-2-propen-1-yl) benzene compound non-containing formula.

What is claimed is:

1. A compound:

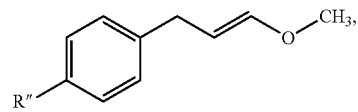

wherein R" represents a $C_2$-$C_4$ alkyl group.

2. The compound of claim 1, wherein the compound is 4-ethyl 1-(3-methoxy-2-propen-1-yl)benzene.

3. The compound of claim 1, wherein the compound is 4-propyl 1-(3-methoxy-2-propen-1-yl)benzene.

4. The compound of claim 1, wherein the compound is 4-isopropyl 1-(3-methoxy-2-propen-1-yl)benzene.

5. The compound of claim 1, wherein the compound is 4-butyl 1-(3-methoxy-2-propen-1-yl)benzene.

6. The compound of claim 1, wherein the compound is 4-sec-butyl 1-(3-methoxy-2-propen-1-yl)benzene.

7. The compound of claim 1, wherein the compound is 4-isobutyl 1-(3-methoxy-2-propen-1-yl)benzene.

8. The compound of claim 1, wherein the compound is 4-tert-butyl 1-(3-methoxy-2-propen-1-yl)benzene.

9. A fragrance formulation containing an olfactory effective amount of a compound:

13
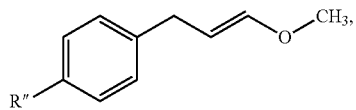
wherein R" represents a $C_2$-$C_4$ alkyl group.
10. A fragrance product containing an olfactory effective amount of the compound:
14
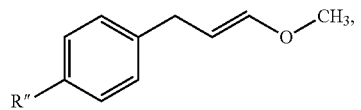
wherein R" represents a $C_2$-$C_4$ alkyl group.
* * * * *